United States Patent
Kimchy et al.

(10) Patent No.: US 11,147,468 B2
(45) Date of Patent: Oct. 19, 2021

(54) POSITION ESTIMATION OF IMAGING CAPSULE IN GASTROINTESTINAL TRACT

(71) Applicant: CHECK-CAP LTD., Isfiya (IL)

(72) Inventors: Yoav Kimchy, Haifa (IL); Boris Karelin, Haifa (IL); Boaz Shpigelman, Netanya (IL); Alex Ovadia, Haifa (IL)

(73) Assignee: CHECK-CAP LTD., Isfiya (IL)

( * ) Notice: Subject to any disclaimer, the term of this patent is extended or adjusted under 35 U.S.C. 154(b) by 390 days.

(21) Appl. No.: 14/785,860

(22) PCT Filed: May 5, 2014

(86) PCT No.: PCT/IL2014/050404
§ 371 (c)(1),
(2) Date: Oct. 21, 2015

(87) PCT Pub. No.: WO2014/195934
PCT Pub. Date: Dec. 11, 2014

(65) Prior Publication Data
US 2016/0066813 A1 Mar. 10, 2016

Related U.S. Application Data

(60) Provisional application No. 61/931,742, filed on Jan. 27, 2014, provisional application No. 61/903,998, (Continued)

(51) Int. Cl.
*A61B 5/06* (2006.01)
*A61B 1/00* (2006.01)
(Continued)

(52) U.S. Cl.
CPC ............ *A61B 5/062* (2013.01); *A61B 1/0002* (2013.01); *A61B 1/00004* (2013.01); (Continued)

(58) Field of Classification Search
None
See application file for complete search history.

(56) References Cited

U.S. PATENT DOCUMENTS 5,604,531 A 2/1997 Iddan et al.
5,676,673 A * 10/1997 Ferre .................. A61B 34/20
606/130

(Continued)

FOREIGN PATENT DOCUMENTS

IL WO 2012056323 A2 * 5/2012 ............. A61B 5/061
JP 2008-220522 A 9/2008
(Continued)

OTHER PUBLICATIONS

Christopher Konvalin, Compensating for Tilt Hard-Iron and Soft-Iron Effects, Dec. 2009, Sensors Online.*
(Continued)

*Primary Examiner* — Daniel L Cerioni
*Assistant Examiner* — Raymond P Dulman
(74) *Attorney, Agent, or Firm* — Soroker Agmon Nordman

(57) ABSTRACT

A system for estimating the position of an imaging capsule that examines the gastrointestinal tract of a user, including an imaging capsule for examining inside the user; and a recorder for communicating with the imaging capsule from outside the user. The imaging capsule includes a controller for controlling functionality of the imaging capsule, a transceiver for communication with the recorder and a coil for transmission of electromagnetic signals. The recorder includes a controller for controlling functionality of the recorder, a transceiver for communication with the imaging capsule and a coil for receiving electromagnetic signals from the coil of the imaging capsule. Wherein the recorder determines the location of the imaging capsule based on (Continued)

measurements of the amplitude of the electromagnetic signals transmitted by the coil in the imaging capsule.

16 Claims, 6 Drawing Sheets

Related U.S. Application Data filed on Nov. 14, 2013, provisional application No. 61/831,163, filed on Jun. 5, 2013.

(51) Int. Cl.
*A61B 1/04* (2006.01)
*A61B 1/045* (2006.01)
*A61B 5/07* (2006.01)
*A61B 5/00* (2006.01)

(52) U.S. Cl.
CPC .......... *A61B 1/00016* (2013.01); *A61B 1/041* (2013.01); *A61B 1/045* (2013.01); *A61B 5/073* (2013.01); *A61B 5/6833* (2013.01); *A61B 5/7203* (2013.01); *A61B 5/725* (2013.01); *A61B 2562/0219* (2013.01); *A61B 2562/0223* (2013.01); *A61B 2562/162* (2013.01)

(56) References Cited

U.S. PATENT DOCUMENTS

| | | | |
|---|---|---|---|
| 6,161,032 A | 12/2000 | Acker | |
| 6,368,285 B1* | 4/2002 | Osadchy | A61B 5/0064 382/131 |
| 7,652,468 B2* | 1/2010 | Kruger | A61B 5/06 324/207.12 |
| 7,844,415 B1* | 11/2010 | Bryant | G01C 25/005 702/151 |
| 2002/0026118 A1* | 2/2002 | Govari | A61B 5/0422 600/462 |
| 2002/0099310 A1 | 7/2002 | Kimchy | |
| 2002/0151808 A1* | 10/2002 | Schwartzman | A61B 5/04011 600/512 |
| 2003/0114742 A1* | 6/2003 | Lewkowicz | A61B 1/00147 600/407 |
| 2004/0097805 A1* | 5/2004 | Verard | A61B 1/00071 600/428 |
| 2004/0138552 A1* | 7/2004 | Harel | A61B 1/00158 600/407 |
| 2004/0243148 A1* | 12/2004 | Wasielewski | A61B 17/00 606/130 |
| 2006/0183993 A1 | 8/2006 | Horn | |
| 2006/0195015 A1 | 8/2006 | Mullick et al. | |
| 2007/0066882 A1* | 3/2007 | Maschke | A61B 5/06 600/407 |
| 2007/0167743 A1* | 7/2007 | Honda | A61B 1/041 600/424 |
| 2008/0039687 A1 | 2/2008 | Shimzu et al. | |
| 2008/0108872 A1* | 5/2008 | Glukhovsky | A61B 1/041 600/117 |
| 2009/0131784 A1* | 5/2009 | Betesh | A61B 1/00016 600/424 |
| 2009/0264778 A1* | 10/2009 | Markowitz | A61B 5/0422 600/508 |
| 2010/0222670 A1 | 9/2010 | Demierre | |
| 2011/0282147 A1* | 11/2011 | Hasegawa | A61B 1/00009 600/109 |
| 2015/0238118 A1* | 8/2015 | Legassey | A61B 5/062 600/347 |
| 2015/0342501 A1* | 12/2015 | Di Natali | A61B 1/00158 600/424 |

FOREIGN PATENT DOCUMENTS

| | | |
|---|---|---|
| JP | 2008-237640 A | 10/2008 |
| JP | 2009-521977 A | 6/2009 |
| WO | 2012/056323 | 5/2012 |

OTHER PUBLICATIONS

Christopher Kovalin, Compensating for Tilt Hard-Iron and Soft-Iron Effects, Dec. 2009, Sensors Online.*

* cited by examiner

POSITION ESTIMATION OF IMAGING CAPSULE IN GASTROINTESTINAL TRACT

RELATED APPLICATIONS

The present application claims priority from U.S. Provisional application No. 61/831,163 filed on Jun. 5, 2013, 61/903,998 filed on Nov. 14, 2013 and 61/931,742 filed on Jan. 27, 2014 the disclosures of which are incorporated herein by reference.

TECHNICAL FIELD

The present disclosure relates generally to investigating the insides of a patient's colon using an intra-lumen capsule and more specifically to estimating the position of the capsule as it traverses the gastrointestinal tract.

BACKGROUND

One method for examining the gastrointestinal tract for the existence of polyps and other clinically relevant features that may provide an indication regarding the potential of cancer is performed by swallowing an imaging capsule that will travel through the gastrointestinal (GI) tract and viewing the patient's situation internally. In a typical case the trip can take between 24-48 hours, after which the imaging capsule exits in the patient's feces. Typically the patient swallows a contrast agent to enhance the imaging ability of the imaging capsule. Then the patient swallows the imaging capsule to examine the gastrointestinal tract while flowing through the contrast agent. The imaging capsule typically includes a radiation source, for example including a radioisotope that emits X-rays or Gamma rays. The radiation is typically collimated to allow it to be controllably directed in a specific direction during the imaging process. In some cases the imaging capsule is designed to measure Compton back-scattering and/or X-ray florescence and wirelessly transmit the measurements (e.g. a count rate) to an external analysis device, for example a computer or other dedicated instruments.

In a typical implementation a radio-opaque contrast agent is used so that a position with a polyp will have less contrast agent and will measure a larger back-scattering count to enhance accuracy of the measurements. Alternatively, other methods may be used to image the gastrointestinal tract.

U.S. Pat. No. 7,787,926 to Kimchy, the disclosure of which is incorporated herein by reference, describes details related to the manufacture and use of such an imaging capsule.

The use of the imaging capsule exposes the user to radiation, which is potentially harmful. Accordingly, it is of interest to limit the user's exposure to radiation when not necessary, for example by radiating only when required and blocking the release of radiation from the capsule when not required. The imaging capsule may be designed with a concealment mechanism that can be instructed to block radiation when not needed for scanning. Optionally, the concealment mechanism would normally be in the closed position, preventing radiation from exiting the capsule when it is not scanning.

In a typical embodiment the imaging capsule can be instructed to selectively scan with radiation only when the capsule changes its position in the colon, since there is no need to repeatedly scan the same position. The use of selective scanning can also preserve energy, thus prolonging the life of the battery and/or enabling the use of a smaller size battery.

It is thus desirable to continuously keep track of the position of the capsule so that the capsule can be instructed to radiate when the position changes or the capsule reaches specific locations of interest. Additionally, tracking the location of the capsule as it traverses through the gastrointestinal tract can help in forming an accurate three dimensional map to assist in locating and treating polyps or other obstructions that are detected.

SUMMARY

An aspect of an embodiment of the disclosure relates to a system and method for estimating the position of an imaging capsule inside the body of a user. The system includes an imaging capsule that is swallowed by the user and a recorder that is positioned outside on the user's body, for example on the user's back or on a belt at the waist. The imaging capsule includes a controller to control functionality of the imaging capsule and a transceiver to communicate with the recorder to receive instructions or provide information. Additionally, the imaging capsule includes a coil to transmit an electromagnetic signal, for example having a low frequency.

The recorder also includes a controller to control its functionality and a transceiver to communicate with the imaging capsule. Additionally, the recorder includes one or more coils to receive the electromagnetic signal transmitted by the imaging capsule.

The controller of the recorder is programmed to analyze the amplitude of the received electromagnetic signal and determine the location of the imaging capsule based on the electromagnetic signal.

In some embodiments of the disclosure, the coil in the imaging capsule may be a single dimension coil with windings in a single plane or it may have windings in two or three planes orthogonal to each other (2D or 3D). Likewise the coil in the recorder may have windings in a single plane or in two or three orthogonal planes.

In an exemplary embodiment of the disclosure, the coil in the imaging capsule has a 3D coil and is designed to transmit simultaneously in three orthogonal directions in different frequencies. Alternatively, the coil in the imaging capsule may transmit sequentially in the three orthogonal directions.

In an exemplary embodiment of the disclosure, the recorder has at least two 3D coils to receive the transmitted signals by the coil of the imaging capsule and determine the location of the imaging capsule based on the transmissions.

In an exemplary embodiment of the disclosure, the imaging capsule and the recorder both include an accelerometer and a magnetometer that identify motion of the imaging capsule. Optionally, the readings of the accelerometer and magnetometer in the imaging capsule are transmitted to the recorder via the transceiver and compared to the readings of the accelerometer and magnetometer of the recorder to identify the spatial orientation of the imaging capsule. In an exemplary embodiment of the disclosure, the spatial orientation is used with the amplitude of the electromagnetic signal received by the coil of the recorder to determine the location of the imaging capsule relative to the recorder and the distance between them.

There is thus provided according to an exemplary embodiment of the disclosure, a system for estimating the position of an imaging capsule that examines the gastrointestinal tract of a user, comprising:

an imaging capsule for examining inside the user; and
a recorder for communicating with the imaging capsule from outside the user;
the imaging capsule, comprising:
a controller for controlling functionality of the imaging capsule;
a transceiver for communication with the recorder;
a coil for transmission of electromagnetic signals, the recorder comprising:
a controller for controlling functionality of the recorder;
a transceiver for communication with the imaging capsule;
a coil for receiving electromagnetic signals from the coil of the imaging capsule;
wherein the recorder determines the location of the imaging capsule based on measurements of the amplitude of the electromagnetic signals transmitted by the coil in the imaging capsule.

In an exemplary embodiment of the disclosure, the coil in the imaging capsule is a 3D coil having windings in three orthogonal directions that transmit simultaneously in three different frequencies. Alternatively, the coil in the imaging capsule is a 3D coil having windings in three orthogonal directions that transmit sequentially.

In an exemplary embodiment of the disclosure, the recorder comprises at least two 3D coils having windings in three orthogonal directions and determines the location of the imaging capsule by detecting a direction in which the amplitudes of the at least two 3D coils are in agreement. Optionally, the agreement takes into account the position difference between the at least two 3D coils.

In an exemplary embodiment of the disclosure, the imaging capsule and the recorder both include a magnetometer and an accelerometer. Optionally, the imaging capsule uses the transceiver to communicate readings from the magnetometer and/or the accelerometer to the recorder. In an exemplary embodiment of the disclosure, the readings are communicated with a time stamp. Optionally, the recorder determines the spatial orientation of the imaging capsule based on the readings of the magnetometer and accelerometer received from the imaging capsule. In an exemplary embodiment of the disclosure, the recorder determines the location of the imaging capsule based on the determined spatial orientation and based on the transmissions of the coil of the imaging capsule. Optionally, the system further comprises a reference patch with similar elements as the imaging capsule; wherein the reference patch is attached to the body of the user and the recorder compares readings from the imaging capsule with readings from the reference patch to eliminate errors resulting from movements of the recorder. In an exemplary embodiment of the disclosure, the recorder uses an adaptive filter to improve the signal to noise ratio of the transmissions received from the coil of the imaging capsule. Optionally, the coil in the imaging capsule includes windings in a single plane. In an exemplary embodiment of the disclosure, the coil in the recorder is a 3D coil having windings in three orthogonal directions.

There is thus further provided according to an exemplary embodiment of the disclosure, a method of estimating the position of an imaging capsule that examines the gastrointestinal tract of a user, comprising:
swallowing an imaging capsule to examine inside the user;
attaching a recorder for communicating with the imaging capsule outside on the body of the user;
programming a controller in the imaging capsule to control functionality of the imaging capsule and a controller in the recorder to control functionality of the recorder;
communicating information between the controller of the imaging capsule and the controller of the recorder using a transceiver in the imaging capsule and a transceiver in the recorder;
transmitting electromagnetic signals from a coil in the imaging capsule;
receiving the electromagnetic signals by a coil in the recorder;
analyzing the amplitude of the electromagnetic signals transmitted by the coil to determine the location of the imaging capsule.

In an exemplary embodiment of the disclosure, the coil in the imaging capsule is a 3D coil having windings in three orthogonal directions that transmit simultaneously in three different frequencies. Alternatively, the coil in the imaging capsule is a 3D coil having windings in three orthogonal directions that transmit sequentially. Optionally, the recorder comprises at least two 3D coils having windings in three orthogonal directions and determines the location of the imaging capsule by detecting a direction in which the amplitudes of the at least two 3D coils are in agreement. In an exemplary embodiment of the disclosure, the imaging capsule and the recorder both include a magnetometer and an accelerometer. Optionally, the imaging capsule uses the transceiver to communicate readings from the magnetometer and/or the accelerometer to the recorder.

BRIEF DESCRIPTION OF THE DRAWINGS

The present disclosure will be understood and better appreciated from the following detailed description taken in conjunction with the drawings. Identical structures, elements or parts, which appear in more than one figure, are generally labeled with the same or similar number in all the figures in which they appear, wherein.

DETAILED DESCRIPTION

Figure 1:
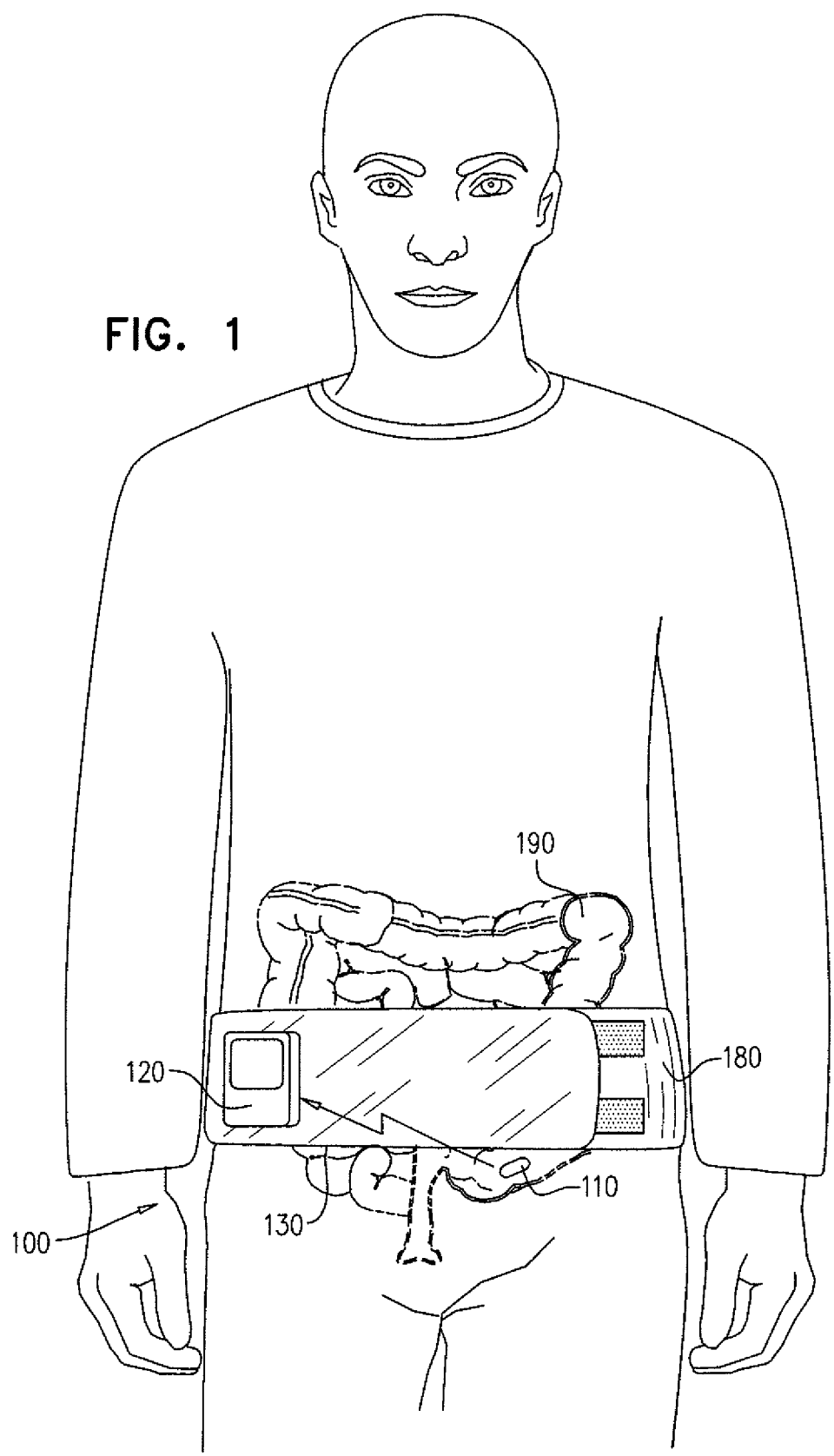
FIG. 1 is a schematic illustration of a system for estimating the position of an imaging capsule inside the body of a user, according to an exemplary embodiment of the disclosure.

FIG. 1 is a schematic illustration of a system 100 for estimating the position of an imaging capsule 110 inside the body of a user. In an exemplary embodiment of the disclosure the user swallows imaging capsule 110. The capsule enters the Gastro Intestinal tract and is especially useful in taking images and mapping the small intestine and colon 190. In an exemplary embodiment of the disclosure, system 100 includes a recorder 120 to communicate 130 with imaging capsule 110 and record information provided by imaging capsule 110. Optionally, the recorder is coupled to a strap or belt 180 to keep it fixated to the user's body in proximity to the small intestine and colon 190 as they are examined by imaging capsule 110. The recorder may be positioned on the front of the user, the back of the user or in any selected position. Optionally, the position is selected empirically to provide optimal readings from transmissions provided by imaging capsule 110. In an exemplary embodiment of the disclosure, recorder 120 analyzes transmissions from image capsule 110 to determine the spatial position of imaging capsule 110 relative to recorder 120.

Figure 2:
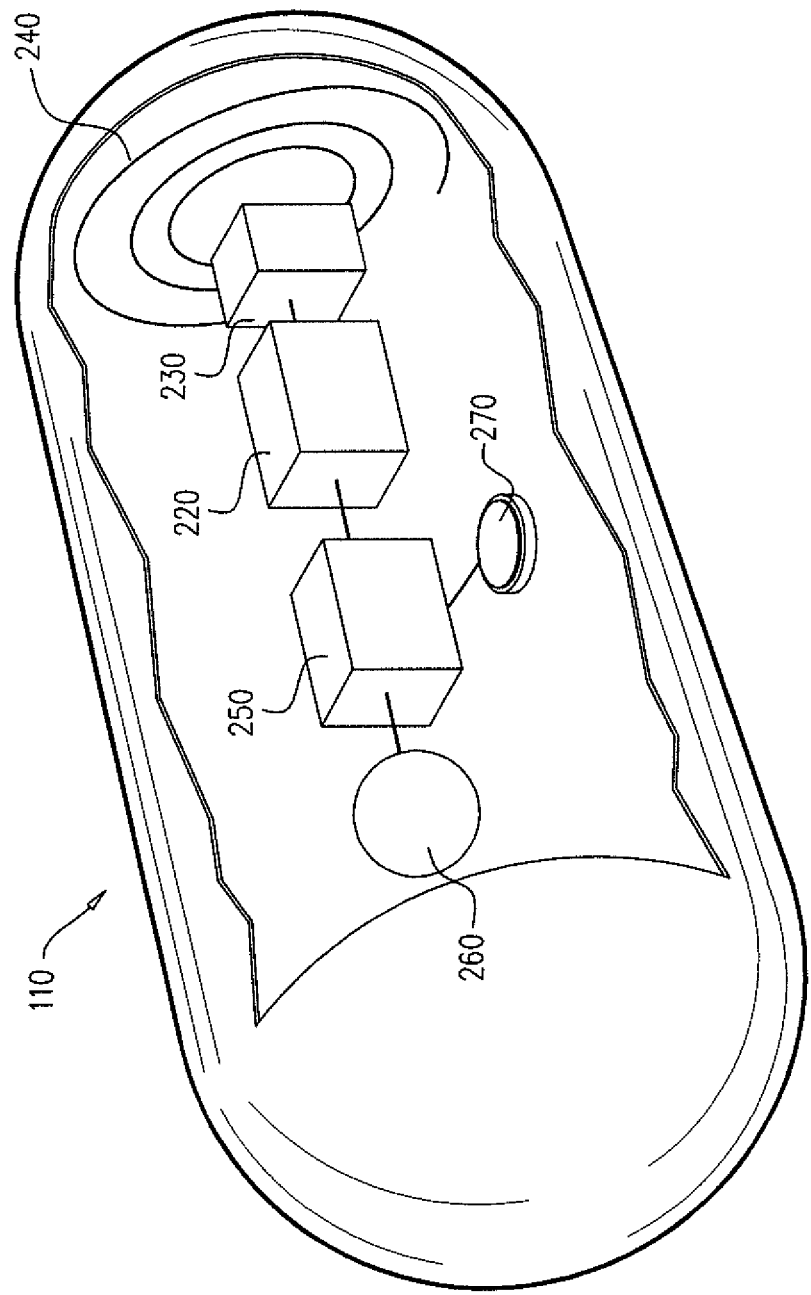
FIG. 2 is a schematic illustration of an imaging capsule, according to an exemplary embodiment of the disclosure.

FIG. 2 is a schematic illustration of imaging capsule 110, according to an exemplary embodiment of the disclosure. Optionally, capsule 110 includes a coil 240 for transmitting a low frequency electromagnetic wave, for example at 1-50 Khz. Alternatively, the transmission of electromagnetic signal may be at approximately 7-14 MHz and the signal can then be used for both localization and data transmission, for example using a communication system on a chip such as NxH2180 manufactured by NXP Semiconductors from Eindhoven, The Netherlands With this implementation, the communication information will be extracted from the coil with a good signal to noise ratio (SNR).

The transmissions are received by recorder 120 and their amplitudes are analyzed to determine the location of imaging capsule 110. In some embodiments of the disclosure, the windings of coil 240 reside in a single plane. Alternatively, coil 240 may include windings in two or three orthogonal planes (a coil with windings in two orthogonal planes is referred to as a 2D coil and a coil with windings in three orthogonal planes is referred to as a 3D coil). Optionally, a 3D coil transmits in three orthogonal directions and uses more energy than a coil transmitting in a single plane. Accordingly, in some embodiments of the disclosure, imaging capsule 110 may be designed to use a single plane coil 240 to conserve power (e.g. provided by a battery 270), and to enable a relatively large coil that improves power efficiency. Whereas recorder 120 that is located outside the user's body may use a 3D coil since its power source can be larger and can easily be replaced if necessary.

In an exemplary embodiment of the disclosure, imaging capsule 110 includes a magnetometer 230 that functions as a 3D geomagnetic sensor (e.g. MAG3110 manufactured by Freescale Semiconductors Ltd from Austin Tex.). Alternatively or additionally, imaging capsule 110 includes an accelerometer 220 that functions to sense changes in the position of imaging capsule 110, for example in colon 190. MMA7260QT manufactured by Freescale Semiconductors LTD is an example of a small sized accelerometer that can be incorporated into imaging capsule 110. In some embodiments of the disclosure, a combined magnetometer and accelerometer can be used, for example FXOS8700CQ manufactured by Freescale Semiconductors LTD.

In an exemplary embodiment of the disclosure, imaging capsule 110 includes a controller 250 and a transceiver 260 to control the functionality of imaging capsule 110 and communicate with recorder 120. The controller 250 may include a processor and/or memory to receive and execute software instructions. Optionally, controller 250 can receive instructions via transceiver 260, for example to start scanning and to stop scanning. Additionally, controller 250 can transmit images recorded by imaging capsule 110 and information regarding the spatial position of the imaging capsule 110, for example the readings of the magnetometer 230 and/or the accelerometer 220. Optionally, the information can notify recorder 120 regarding the orientation of imaging capsule 110 and coil 240 relative to the magnetic field and gravitational field of the earth.

Figure 3:
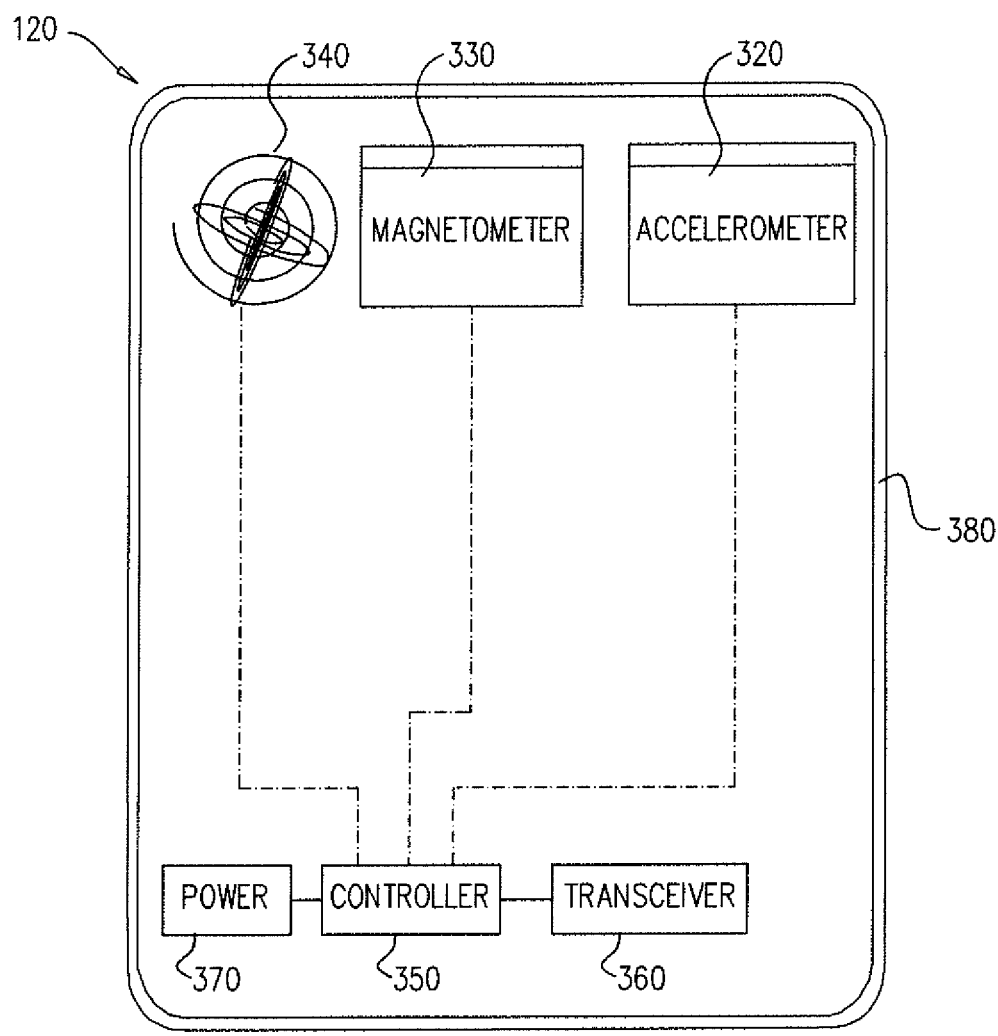
FIG. 3 is a schematic illustration of a recorder, according to an exemplary embodiment of the disclosure.

FIG. 3 is a schematic illustration of recorder 120, according to an exemplary embodiment of the disclosure. Optionally, recorder 120 may include a controller 350, a transceiver 360, a magnetometer 330, an accelerometer 320, a power source 370 and one or more reception coils 340. Optionally, the one or more reception coils 340 may be single plane coils or have windings in two or three orthogonal planes (a 2D coil or a 3D coil). In an exemplary embodiment of the disclosure, one or more reception coils 340 of recorder 120 interact with coil 240 of imaging capsule 110 by receiving the low frequency transmissions transmitted from the imaging capsule 110. Optionally, analysis of the amplitude of the transmissions from imaging capsule 110 by a combination of reception coils 340 can be used to determine the direction and distance from recorder 120 so that the spatial location of the imaging capsule 110 can be calculated and the distance between the recorder 120 and the imaging capsule 110 can be determined.

In an exemplary embodiment of the disclosure, readings from magnetometer 230 and/or accelerometer 220 are transmitted from imaging capsule 110 to recorder 120. Optionally, recorder 120 compares the readings with the readings of magnetometer 330 and/or accelerometer 320 to determine the angular direction of imaging capsule 110 and coil 240 relative to the direction of recorder 120 and the one or more reception coils 340. In an exemplary embodiment of the disclosure, the readings of magnetometer 230 and/or accelerometer 220 are transmitted with a timestamp from imaging capsule 110 to synchronize comparison of the readings of magnetometer 230 and/or accelerometer 220 with the readings of magnetometer 330 and/or accelerometer 320. Optionally, the amplitudes measured by the one or more reception coils 340 from the transmissions of coil 240 with the angular direction determined from the readings of magnetometer 230 and/or accelerometer 220 are used to determine the spatial location of imaging capsule 110 relative to recorder 120.

In an exemplary embodiment of the disclosure, electromagnetic disturbances to the transmissions of coil 240 can be identified, for example by controller 350 of recorder 120 since the spatial angles of imaging capsule 110 are acquired by magnetometer 330 and/or accelerometer 320. Optionally, in the case of an external magnetic or metallic disturbance the electromagnetic field will be disturbed differently then the constant earth magnetic field and/or the gravitational field. Therefore a sudden change in the amplitude of the transmissions from coil 240 without a matching change in the spatial orientation of the imaging capsule as recorded by the magnetometer 330 and/or accelerometer 320 can provide an indication regarding an electromagnetic disturbance that can be disregarded. In some embodiments of the disclosure, the coil amplitude will be processes only when movement of the imaging capsule 110 is detected.

In an exemplary embodiment of the disclosure, the distance to the imaging capsule 110 is calculated using two or more reception coils 340 at recorder 120 without information from accelerometer 220 and/or magnetometer 230. In an exemplary embodiment of the disclosure, the two or more reception coils may have windings in a single plane or may have windings in two or three orthogonal planes. In some embodiments of the disclosure at least one of the reception coils 340 is a 3D coil. Optionally, the position is determined by testing all possible directions for the imaging capsule 110 and selecting the direction for which the two or more reception coils 340 reach agreement for the calculated position of the imaging capsule 110. Optionally, the agreement takes into account the position difference between the two or more reception coils 340 in recorder 120. In an exemplary embodiment of the disclosure, one of the reception coils 340 may serve as a transmitter and receiver to provide transmissions to the other reception coils 340 so that the relative distance and angles between the reception coils 340 in the recorder 120 can be measured before calculating the distance to coil 240. Alternatively, a separate transmitting reference coil is used and distance is calculated relative to that reference.

In some embodiments of the disclosure, coil 240 in imaging capsule 110 is a 3D coil that transmits simultaneously in three different frequencies, or alternatively transmits with a single frequency but the windings of each orthogonal plane transmit sequentially so that the receiver can distinguish between the three transmissions. Optionally, a single planar reception coil 340 may be used to receive the transmissions and calculate the distance from recorder 120 and imaging capsule 110 at that moment.

In an exemplary embodiment of the disclosure, recorder 120 includes an encasement 380 (FIG. 3). Optionally, encasement 380 is coated with a high permeability material that shields the elements of recorder 120 from the influence of magnetic fields outside the body, for example such as MuMetal manufactured by The MuShield Company from Londonderry, N.H., USA. In an exemplary embodiment of the disclosure, the side facing the user's body is not coated so that it can receive transmissions from imaging capsule 110 from inside the user's body. Optionally, the effect of the shielding if any is calibrated by recorder 120 so that it is shielded from external electromagnetic interference.

Figure 4:
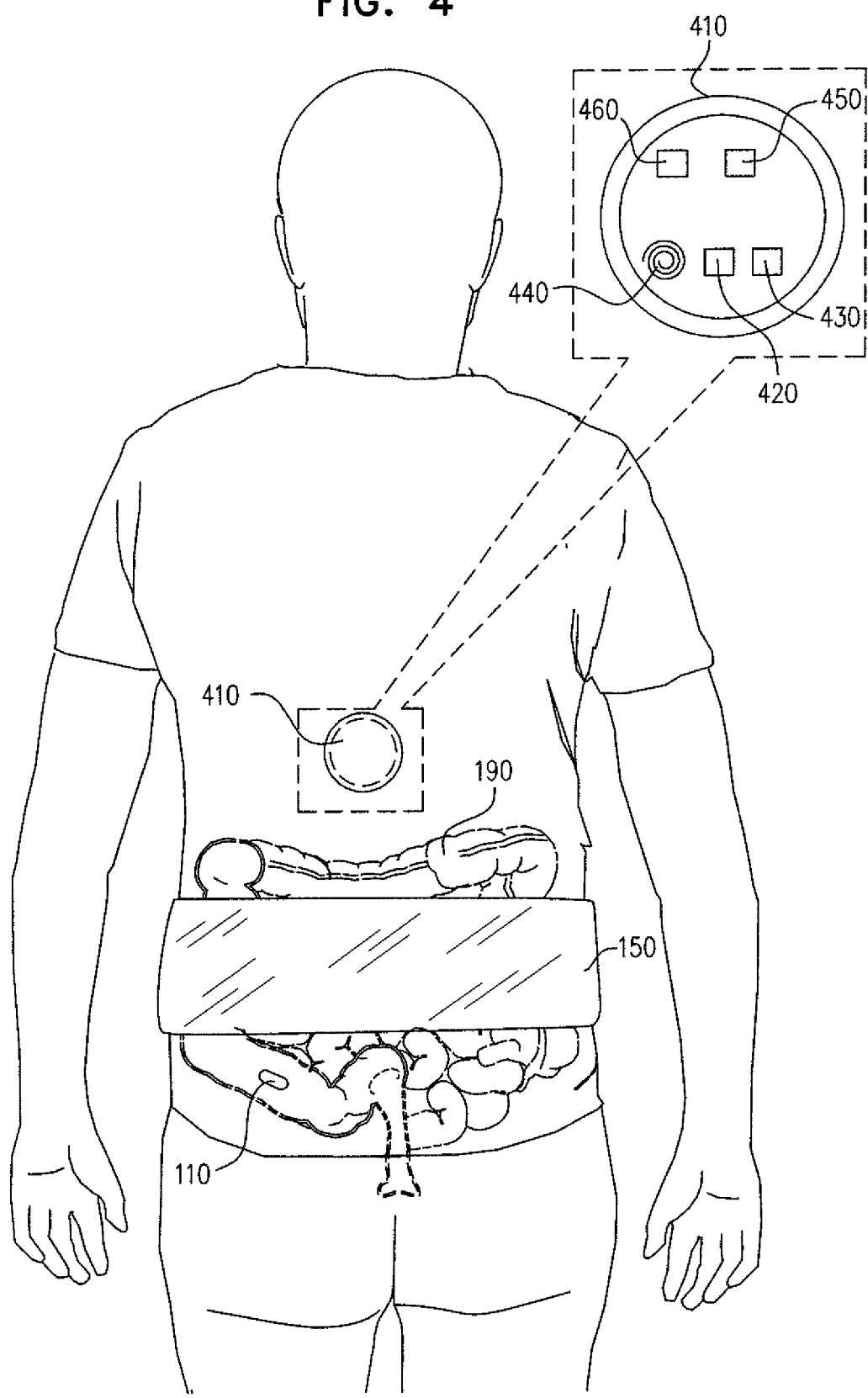
FIG. 4 is a schematic illustration of a reference patch for use with a system for estimating the position of an imaging capsule, according to an exemplary embodiment of the disclosure.

FIG. 4 is a schematic illustration of a reference patch 410 for use with system 100 for estimating the position of imaging capsule 110. In an exemplary embodiment of the disclosure, reference patch 410 is small like imaging capsule 110 and includes similar elements, for example an accelerometer 420, a magnetometer 430, a coil 440, a controller 450 and a transceiver 460. Optionally, reference patch 410 is attached to the user, for example adhesively positioned on the user's back. The reference patch 410 serves as a stationary reference in contrast to imaging capsule 110 that dynamically moves through the user's gastro intestinal tract. Optionally, recorder 120 communicates with reference patch 410 and with imaging capsule 110.

In an exemplary embodiment of the disclosure, recorder 120 calculates the position of the imaging capsule 110 relative to reference patch 410 to reduce recording false movements resulting from movements of recorder 120 which is optionally, larger and bulkier than reference patch 410 and more susceptible to movements since it may be attached to belt 180 and not adhesively attached to the body of the user. In some embodiments of the disclosure, recorder 120 may be implemented in the form of reference patch 410 (e.g. in the form of a small patch attached to the user as shown in FIG. 4) instead of in the form of recorder 120 as shown in FIG. 1, so that recorder 120 only needs to communicate with imaging capsule 110 and not with an additional reference patch. In some embodiments of the disclosure, reference patch 410 may also transmit signals from coil 440 to imaging capsule 110, for example to test the communication range.

Figure 5:
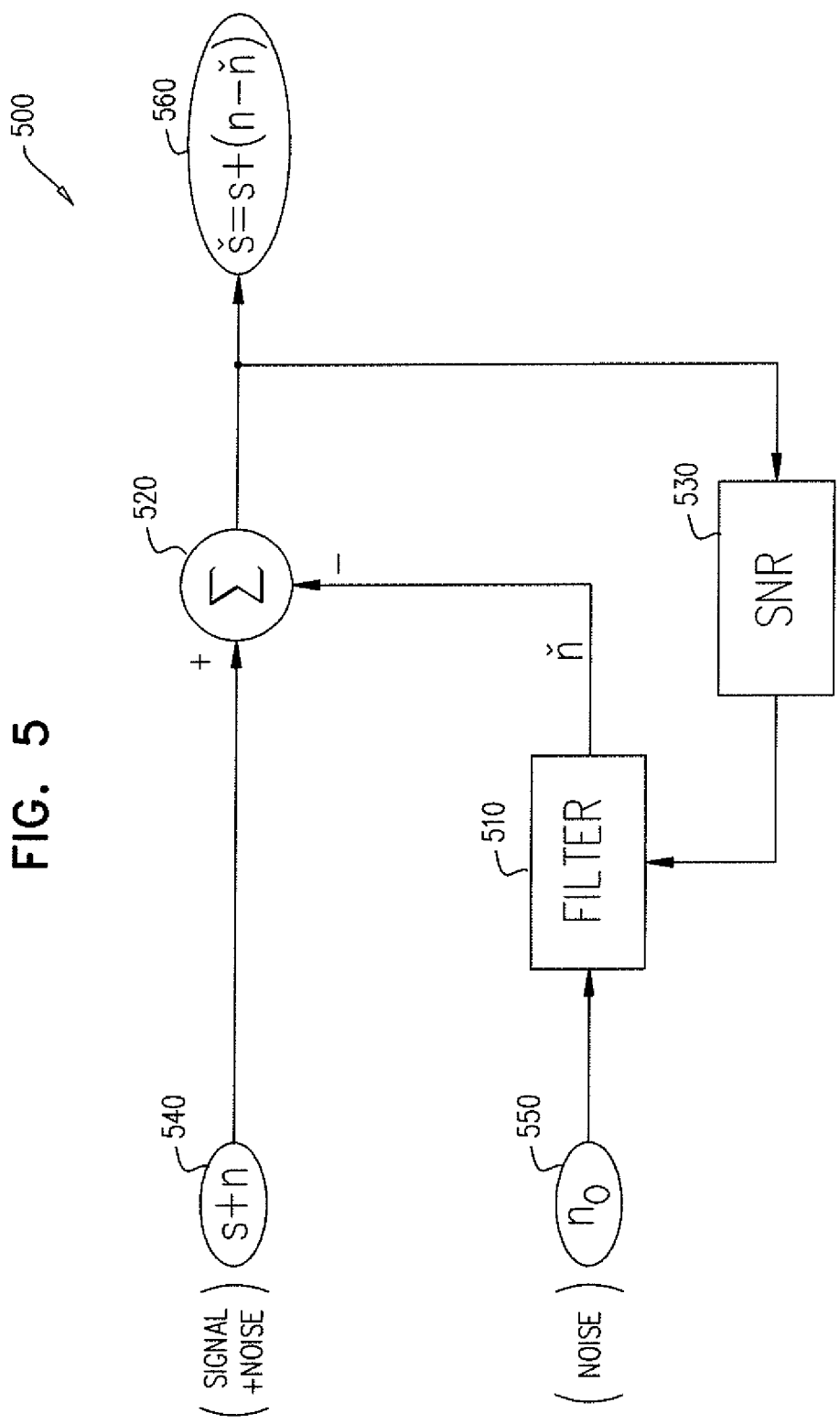
FIG. 5 is a schematic illustration of an adaptive filter for improving the accuracy in estimating the position of an imaging capsule, according to an exemplary embodiment of the disclosure.

FIG. 5 is a schematic illustration of an adaptive filter 500 for improving the accuracy in estimating the position of imaging capsule 110. In an exemplary embodiment of the disclosure, recorder 120 uses an adaptive filter (e.g. in controller 350) to reduce noise and improve the signal to noise ratio (SNR) in the transmissions received from imaging capsule 110 (e.g. from the signals received by reception coils 340). Optionally, by estimating the noise in the environment while the imaging capsule 110 is not transmitting, adaptive filter 500 can be set to reduce the noise (assuming that the noise while imaging capsule 110 is transmitting is similar to the noise when it is not transmitting). In an exemplary embodiment of the disclosure, a signal received by recorder 120 from imaging capsule 110 (including noise) is fed into an input 540 of adaptive filter 500. Optionally, the estimated noise measured while imaging capsule 110 is not transmitting is recorded and fed into a noise input 550. A filter 510 accepts the signal from noise input 550 and prepares it for combining with the input signal to cancel out the noise from the input signal. A summator 520 combines the input signal with the processed noise and provides the combined signal to an output 560 as an output signal. Additionally, the output signal is provided as feedback via a signal to noise ratio controller 530 to filter 510 to improve processing of the input signal and maximize the signal to noise ratio.

Following is a description of an exemplary closed form analytic solution to calculate the distance from recorder 120 to imaging capsule 110, according to an exemplary embodiment of the disclosure Optionally, in this calculation the spatial location of imaging capsule 110 relative to recorder 120 is known from the readings of accelerometer 220, accelerometer, 320, magnetometer 230, magnetometer 330, coil 240 with windings in one to three orthogonal planes and one reception coil 340 with windings in three orthogonal planes.

Induction coil 240 generates a low-frequency magnetic field having the vector amplitude $B=(B_x, B_y, B_z)$ described by the magnetic dipole:

$$B = \beta \frac{3(n, r')r - |r|^2 n}{|r|^5}; \quad \text{Equation (1)}$$

Where n is the capsule coil normal vector (representing the transmission from coil 240) and r is the radius vector of the coil center.

The amplitude induced on the i-th coil in the receiver is:

$$V_i = \alpha_i(B, n_i^r), i=1,2,3; \quad \text{Equation (2)}$$

where $n_i$ is the i-th coil normal vector.

$$\beta = \frac{\mu_0 I_c N_c \pi a_c^2}{4\pi}$$

where $\mu_0 = 4\pi \cdot 10^{-7}$ Vs/(Am) is the magnetic permeability of vacuum, $I_c$ is the electric current in the capsule coil, $N_c$ is the number of capsule coil turns, $a_c$ is the capsule coil effective radius, $n=(n_x, n_y, n_z)$ is the capsule coil normal vector and $r=(x-x_0, y-y_0, z-z_0)$ is the Cartesian distance vector between the observation point $(x_0, y_0, z_0)$ and the capsule coil center $(x, y, z)$.

$$\alpha_i = 2\pi f N_i \mu a_i^2$$

where f is the field frequency, $N_i$ is the i-th coil number of turns, $a_i$ is the i-th coil effective radius, $n_i=(n_{xi}, n_{yi}, n_{zi})$ is the i-th coil normal vector, and $B_i$ is the magnetic field at the i-th coil center.

Now we go to calculate vector r from the known amplitude values and the coil normal vectors. First of all one can see that if r is a solution then $-r$ is a solution as well. We can choose usually the proper solution from the physical issues and/or from the history of the tracking.

By substituting equation (1) to (2) we obtain:

$$V_i = \alpha_i \left( \beta \frac{3(n, r^t)r - |r|^2 n}{|r|^5}, n_i^t \right) = \alpha_i \beta \left( \frac{3(n, \rho^t)\rho - n}{|r|^3}, n_i^t \right)$$

Here $\rho$ is the normalized vector r.
Accordingly:

$$\frac{|r|^3}{\alpha_i \beta} V_i = n(3\rho^t \rho - I) n_i^t$$

Let $$N = [n_1^t \quad n_2^t \quad n_3^t]$$

$$V = \left[ \frac{V_1}{\alpha_1} \quad \frac{V_2}{\alpha_2} \quad \frac{V_3}{\alpha_3} \right] = BN$$

Then we obtain:

$$\frac{|r|^3}{\beta} V = n(3\rho^t \rho - I)N$$

$$\frac{|r|^3}{\beta} V N^{-1} = n(3\rho^t \rho - I)$$

Now we define (m) and receive equation (3) by substitution:

$$m = \frac{1}{\beta} V N^{-1} = \frac{1}{\beta} B \quad (3)$$

$$|r|^3 m = n(3\rho^t \rho - I)$$

Figure 6:
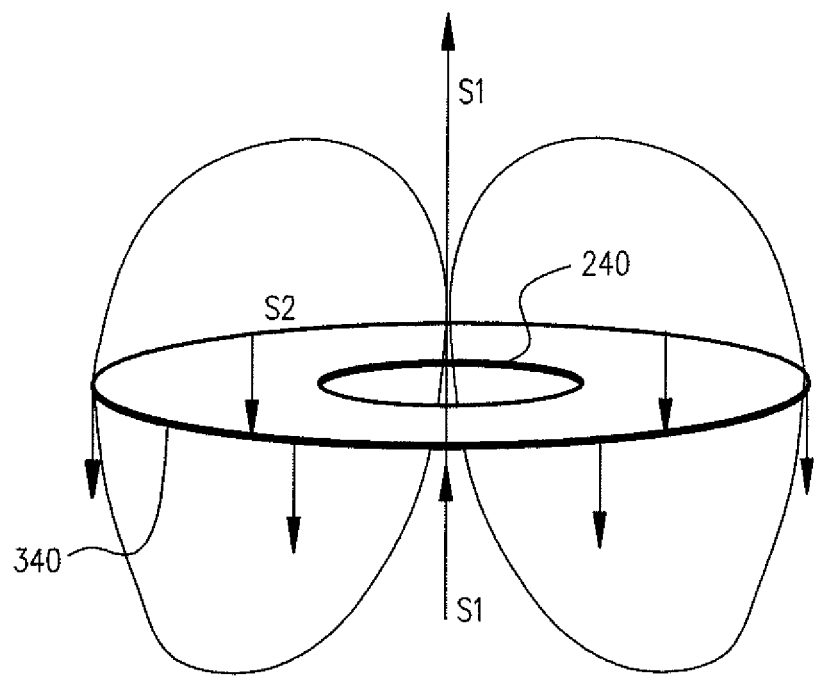
FIG. 6 is a schematic illustration of magnetic fields transmitted and received by an imaging capsule and a recorder, according to an exemplary embodiment of the disclosure.

Let us consider the special case as illustrated by FIG. 6, wherein the normal vector of the transmission by coil 240 (n) and the normal vector of the reception by coil 340 (m) are parallel (i.e. m↑↑n) and designated as (S) with 2 sub-cases (S1) and (S2) (parallel and anti-parallel).

This means that the magnetic field B is parallel to the capsule direction n, B=kn. One can see from (1) above that:

$$B = kn = \beta \frac{3(n, r^t)r - |r|^2 n}{|r|^5},$$

$$\beta \frac{3(n, r^t)\rho}{|r|^3} = \tilde{k}n$$

We represent $$\rho = \tau n + \varphi n^-, \langle n, n^- \rangle = 0$$

And obtain from this $$\tilde{k}n = \beta \frac{3\tau(\tau n + \varphi n^-)}{|r|^3},$$

$$\tau\varphi = 0$$

Thus the case (S) may be divided to two sub-cases:

$$\rho = \pm n \quad (S1)$$

$$\langle \rho, n \rangle = 0 \quad (S2)$$

For S1 the formula looks like this:

$$B = \beta \frac{3\rho - n}{|r|^3} = \beta \frac{2n}{|r|^3}$$

$$r = \pm \sqrt[3]{\frac{2\beta}{|B|}} n$$

And for S2 we get:

$$B = \beta \frac{-n}{|r|^3},$$

$$|r| = r_0 = \sqrt[3]{\frac{\beta}{|B|}}$$

As shown in FIG. 6 $r_0$ is the radius of the circle (O) with the center in the origin and oriented orthogonally to n. Then every point in O is the solution of (1). Accordingly the solution can be found by tracking the received amplitudes.

Figure 7:
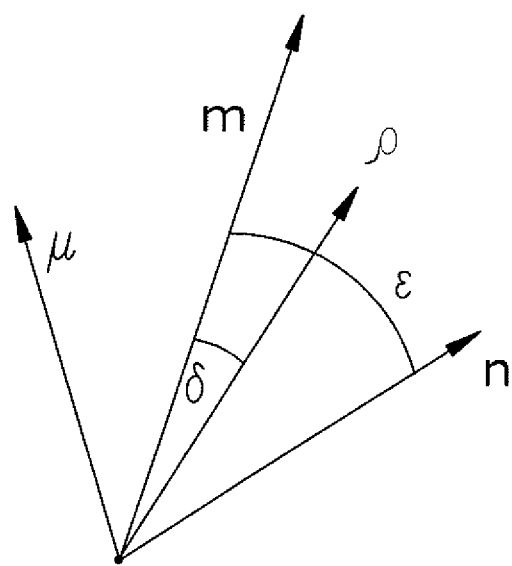
FIG. 7 is a schematic illustration of vectors representing magnetic fields transmitted and received by an imaging capsule and a recorder, according to an exemplary embodiment of the disclosure.

FIG. 7 illustrates the normal vector of the transmission by coil 240 (n) and the normal vector of the reception by coil 340 (m) in the general case when they are not parallel. Accordingly, in the non non-special case (not S). We multiple both sides from the left by $$h = [m, n]$$

$$|r|mh^t = n(3\rho^t \rho - I)h^t$$

$$0 = 3\gamma \rho h^t$$

Here $$\gamma = n\rho^t = \cos \delta$$

We see that vector $\rho$ is co-planar to the vectors n and m. Let $\mu$ be the normalized vector in the plane of m and n which is orthogonal to n.

Let us multiply the equation (3) by n and by μ taking into account the following:

$$\rho\mu^t = \pm\sqrt{1-\gamma^2} = \sin\epsilon$$

Receiving equations (4):

$$|r|^3 mn^t = n(3\rho^t\rho - I)n^t = 3\gamma^2 - 1 = 3\cos^2\delta - 1 \quad (4)$$

$$|r|^3 m\mu^t = n(3\rho^t\rho - I)\mu^t = \pm 3\gamma\sqrt{1-\gamma^2} = 3\cos\delta\sin\delta \quad (4)$$

For $$\eta = nm^t = |m|\cos\epsilon$$

$$\xi = m\mu^t = |m|\sin\epsilon$$

$$(3\gamma^2 - 1)\xi = \pm 3\gamma\sqrt{1-\gamma^2}\eta \quad (5)$$

We take the square of the both sides of (5) and solve the bi-quadratic equation $$a\gamma^4 + b\gamma^2 + c = 0$$

$$a = 9(\xi^2 + \eta^2) = 9m^2$$

$$b = -6\xi^2 - 9\eta^2 = -3m^2(2 + \cos^2\epsilon)$$

$$c = \xi^2 = m^2\sin^2\epsilon$$

with respect to γ. The discriminant $$D = b^2 - 4ac$$
$$= m^4(9(2 + \cos^2\varepsilon)^2 - 36\sin^2\varepsilon)$$
$$= 9m^4((2 + \cos^2\varepsilon)^2 - 4\sin^2\varepsilon)$$
$$= 9m^4(4 + 4\cos^2\varepsilon + \cos^4\varepsilon - 4\sin^2\varepsilon)$$
$$= 9m^4(8\cos^2\varepsilon + \cos^4\varepsilon) > 0$$

Thus there are two real solutions for $\gamma^2$: $g_1$ and $g_2$. We can see from the Vieta formulas that $$g_1 g_2 = \frac{c}{a} = \frac{\sin^2\varepsilon}{9} \leq \frac{1}{9}$$

$$g_1 + g_2 = -\frac{b}{a} = -\frac{-3m^2(2 + \cos^2\varepsilon)}{9m^2} = \frac{(2 + \cos^2\varepsilon)}{3} \geq \frac{2}{3}$$

One can see from (5) as well that $0 \leq \gamma^2 \leq 1$. Finally $$0 \leq g_1 \leq \frac{1}{3} \leq g_2 \leq 1$$

We can choose the solution $g_{1,2}$ for which the expression $$\frac{3g_{1,2} - 1}{\eta} > 0$$

The case η=0 is of special interest. One can see that in this situation $$g_1 = g_2 = \frac{1}{3}, \xi = |m|.$$

Finally we obtain from (4):

$$|r| = \begin{cases} \sqrt[3]{\frac{3g_1 - 1}{\eta}}, \gamma = \sqrt{g_1} & \eta < 0 \\ \sqrt[3]{\frac{\sqrt{2}}{|m|}}, \gamma = \frac{1}{\sqrt{3}} & \eta = 0 \\ \sqrt[3]{\frac{3g_2 - 1}{\eta}}, \gamma = \sqrt{g_2} & \eta > 0 \end{cases}$$

The final step is $$\rho = \pm\frac{1}{3\gamma}(|r|^3 m + n)$$

Accordingly, the value of p provides us with the distance.

Optionally, previous position data are used to solve ambiguity relating to special cases, for example using historical positions near the singularity.

It should be appreciated that the above described methods and apparatus may be varied in many ways, including omitting or adding steps, changing the order of steps and the type of devices used. It should be appreciated that different features may be combined in different ways. In particular, not all the features shown above in a particular embodiment are necessary in every embodiment of the disclosure. Further combinations of the above features are also considered to be within the scope of some embodiments of the disclosure. It will also be appreciated by persons skilled in the art that the present disclosure is not limited to what has been particularly shown and described hereinabove.

We claim:

1. A system for estimating the position of an imaging capsule that examines the gastrointestinal tract of a user, comprising;
    an imaging capsule for examining inside the user; and
    a recorder for communicating with the imaging capsule from outside the user; and
    a reference patch;
    the imaging capsule, comprising:
        a controller for controlling functionality of the imaging capsule;
        a transceiver for communication with the recorder;
        a magnetometer and an accelerometer to identify movement;
        a coil configured to generate a low frequency magnetic field,
    the recorder comprising the following elements:
        a controller for controlling functionality of the recorder;
        a transceiver for communication with the imaging capsule and the reference patch;
        a magnetometer and an accelerometer to identify movement;
        at least one coil configured to detect an amplitude of a low frequency magnetic field produced by other coils; wherein all the elements of the recorder are enclosed in an encasement configured to be coupled to a strap, belt or a body of the user to keep the recorder fixed to the body of the user in proximity to the small intestine and colon;

the reference patch comprising:
- a controller for controlling functionality of the reference patch;
- a transceiver for communicating with the recorder;
- a coil configured to generate a low frequency magnetic field;
- wherein the reference patch is configured to be attached to a body of the user at a different position than the coil of the recorder and to be stationary relative to the user, serving as a stationary reference point opposed to the imaging capsule that moves dynamically, and wherein the recorder compares measurements from the coil of the imaging capsule with measurements from the coil of the reference patch to eliminate errors resulting from movement of the encasement of the recorder;
- wherein the identified movement of the imaging capsule and recorder is used to identify electromagnetic disturbances that can be disregarded;
- wherein the recorder is configured to determine a spatial orientation of the imaging capsule relative to the recorder by receiving and comparing measurements of the accelerometer and the magnetometer of the imaging capsule with measurements of the accelerometer and the magnetometer of the recorder;
- wherein the recorder is configured to calculate a distance from the recorder to the imaging capsule and a location of the imaging capsule using the determined spatial orientation and the low frequency magnetic field generated by the coil of the imaging capsule that is detected by the coil of the recorder; and
- wherein the tracking location of the imaging capsule enables forming a three dimensional map to assist in locating and treating polyps or other obstructions that are detected.

2. A system according to claim 1, wherein the coil in the imaging capsule is a three-dimensional (3D) coil having windings in three orthogonal directions that transmit simultaneously in three different frequencies.

3. A system according to claim 1, wherein the coil in the imaging capsule is a three-dimensional (3D) coil having windings in three orthogonal directions that transmit sequentially.

4. A system according to claim 1, wherein the recorder comprises at least two three-dimensional (3D) coils having windings in three orthogonal directions.

5. A system according to claim 4, wherein the recorder further determines the location of the imaging capsule by taking into account the position difference between the at least two three-dimensional (3D) coils.

6. A system according to claim 1, wherein the imaging capsule uses the transceiver to communicate measurements from the magnetometer and/or the accelerometer to the recorder.

7. A system according to claim 6, wherein the measurements are communicated with a time stamp.

8. A system according to claim 1, wherein the recorder uses an adaptive filter to improve a signal to noise ratio of the magnetic field generated by the coil of the imaging capsule.

9. A system according to claim 1, wherein the coil in the imaging capsule includes windings in a single plane.

10. A system according to claim 1, wherein the coil in the recorder is a three-dimensional (3D) coil having windings in three orthogonal directions.

11. A method of estimating the position of an imaging capsule that examines the gastrointestinal tract of a user, comprising:
- swallowing an imaging capsule to examine inside the user, said imaging capsule comprising a radiation source;
- attaching a recorder for communicating with the imaging capsule outside on the body of the user, wherein all the elements of the recorder are enclosed in an encasement configured to be coupled to a strap, belt or a body of the user to keep the recorder fixed to the body of the user in proximity to the small intestine and colon;
- attaching a reference patch to the body of the user at a different position than the coil of the recorder, wherein the reference patch is stationary relative to the user, serving as a stationary reference point opposed to the imaging capsule that moves dynamically;
- programming a controller in the imaging capsule to control functionality of the imaging capsule, a controller of the reference patch to control functionality of the reference patch and a controller in the recorder to control functionality of the recorder;
- communicating information between the controller of the imaging capsule, the controller of the reference patch and the controller of the recorder using a transceiver in the imaging capsule, the reference patch and a transceiver in the recorder;
- generating a low frequency magnetic field with a coil in the imaging capsule and a coil in the reference patch;
- receiving the low frequency magnetic fields in the recorder by a coil that is configured to detect amplitudes of the low frequency magnetic fields;
- determining a spatial orientation of the imaging capsule relative to the recorder by receiving and comparing measurements of an accelerometer and a magnetometer of the imaging capsule with measurements of an accelerometer and a magnetometer of the recorder;
- calculating a distance from the recorder to the imaging capsule and a location of the imaging capsule using the determined spatial orientation and the low frequency magnetic field generated by the coil of the imaging capsule that is detected by the coil of the recorder
- forming a three dimensional map to assist in locating and treating polyps or other obstructions that are detected;
- wherein the accelerometer and magnetometer of the imaging capsule and the accelerometer and magnetometer of the recorder identify movement of the imaging capsule and of the recorder respectively and identify electromagnetic disturbances that can be disregarded.

12. A method according to claim 11, wherein the coil in the imaging capsule is a three-dimensional (3D) coil having windings in three orthogonal directions that transmit simultaneously in three different frequencies.

13. A method according, to claim 11, wherein the coil in the imaging capsule is a three-dimensional (3D) coil having windings in three orthogonal directions that transmit sequentially.

14. A method according to claim 11, wherein the recorder comprises at least two three-dimensional (3D) coils having windings in three orthogonal directions.

15. A method according to claim 11, wherein the imaging capsule uses the transceiver to communicate measurements from the magnetometer and/or the accelerometer to the recorder.

16. A system according to claim 1, wherein the reference patch is further configured to communicate with the recorder and to transmit signals to the imaging capsule, enabling the recorder to compare measurements from the coil of the imaging capsule with measurements from the coil of the reference patch to eliminate errors resulting from movement of the recorder or to test communication range with the imaging capsule.

* * * * *